US006405086B1

(12) United States Patent
Conley et al.

(10) Patent No.: US 6,405,086 B1
(45) Date of Patent: Jun. 11, 2002

(54) KNOWLEDGE SHARING IN SYSTEMS INCLUDING IMPLANTABLE MEDICAL DEVICES

(75) Inventors: Vickie L. Conley, Woodbury; Allan T. Koshiol; Kristine M. Larsen-Kelly, both of Lino Lakes, all of MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 09/382,307

(22) Filed: Aug. 24, 1999

Related U.S. Application Data

(63) Continuation-in-part of application No. 09/379,286, filed on Aug. 22, 1999.

(51) Int. Cl.[7] .......................... A61N 1/362; A61N 1/37

(52) U.S. Cl. .......................................... 607/27; 607/28

(58) Field of Search .................................... 607/27–29

(56) References Cited

U.S. PATENT DOCUMENTS 5,476,485 A * 12/1995 Weinberg et al. ............. 607/28
5,722,999 A * 3/1998 Snell ........................... 607/32
5,891,043 A * 4/1999 Ericksen et al. ............ 600/508
5,891,178 A 4/1999 Mann et al. .................. 607/27
5,944,746 A * 8/1999 Kroll ........................... 607/27
6,021,351 A * 2/2000 Kadhiresan et al. .......... 607/27

FOREIGN PATENT DOCUMENTS

EP 0756877 2/1997 .......... A61N/1/372

* cited by examiner

*Primary Examiner*—Carl Layno
(74) *Attorney, Agent, or Firm*—Schwegman, Lundberg, Woessner & Kluth, P.A.

(57) ABSTRACT

Systems, structures, and methods are provided to share information in systems including implantable medical devices. Information acquired or generated in the systems is made available so that components of the systems or implantable medical devices can use it without having to reacquire such information.

34 Claims, 9 Drawing Sheets

800

START

802 ACQUIRING DATA

804 EXECUTING APPLICATION

806 SHARING KNOWLEDGE

END

KNOWLEDGE SHARING IN SYSTEMS INCLUDING IMPLANTABLE MEDICAL DEVICES

CROSS REFERENCE TO RELATED APPLICATIONS

This application is a continuation-in-part of U.S. patent application Ser. No. 09/379,286, filed on Aug. 22, 1999, the specification of which is incorporated herein by reference.

TECHNICAL FIELD

The present invention relates generally to implantable medical devices. More particularly, it pertains to sharing information based on data acquired in the process of operating implantable medical devices.

BACKGROUND INFORMATION

A normal human heart beats between 60 to 100 times per minute. However, when a person gets excited or frightened or has an illness such as congenital heart disease, the heart may beat faster than 100 times per minute. A disruption in the normal heart rate or rhythm is known as arrhythmia.

Arrhythmias are caused by abnormal functioning of the electrical conduction of the heart. Normally, the chambers of the heart (atria and ventricles) work in a coordinated manner. The electrical conduction begins with an electrical impulse originating in the sinoatrial node. This impulse is then moved through the atria, stimulates them to contract, and then is moved to its final destination at the ventricles, where it stimulates them to contract also. Any problems along this conduction path may cause arrhythmia.

Certain types of arrhythmia are lethal and may cause severe damage to various organs in the body by initially decreasing the pumping of the heart. When the pumping of the heart is decreased by more than a few seconds, blood circulation is essentially stopped, and organ damage (such as brain damage) may occur within a few minutes.

Arrhythmias have been treated by the use of a pacemaker that applies shock therapy. A pacemaker is a medical device that delivers controlled electrical pulses to an electrode that is implanted adjacent to or in the heart. These controlled electrical pulses stimulate the heart so that it will contract and beat at a desired rate. The delivery of these controlled electrical pulses is often tailored to the individual patient.

The process of tailoring a therapy to the specific patient is iteratively performed by a physician. The process involves many tests that must be repeated until the physician can extract operating parameters for the pacemaker. The physician may have to re-enter data for the same test at each repeated interval. This problem has burdened the physician in terms of time. What has also been frustrating is that certain data acquired is needed in other parts of the tailoring process yet this data cannot presently be shared.

Thus, what is needed are systems, structures, and methods to share information in systems including implantable medical devices.

SUMMARY

The above-mentioned problems with the use of data in systems including implantable medical devices as well as other problems are addressed by the present invention and will be understood by reading and studying the following specification. Systems, structures, and methods are described which ease the sharing of data in applications involving an implantable medical device.

In particular, an illustrative embodiment includes an exemplary system that includes an implantable medical device implanted in a patient. The system comprises a first application executing a first diagnostic test. The first application acquires a set of data from the implantable medical device in executing the first diagnostic test. The system further comprises a second application that initiates a second diagnostic test. The first application shares a portion of the data acquired with the second application so that the second application need not acquire the portion of the set of data.

Another illustrative embodiment includes an exemplary system that includes an implantable medical device. The system comprises a database to store a set of data acquired from the implantable medical device. The system further comprises an application executing on the system. The database shares a portion of the set of data acquired in operating the implantable medical device so that the application need not acquire the portion of the set of data.

Another illustrative embodiment includes an exemplary system that includes an implantable medical device. The system comprises an information miner to mine information generated in the system. The system further comprises an application executing on the system. The desire of the application for a portion of the information mined by the information miner is detected. The information miner shares the portion of the information it has mined so that the application need not acquired the portion of the information.

Another illustrative embodiment includes an exemplary method of sharing information in a system that includes an implantable medical device. The method comprises acquiring a set of data, executing an application, and sharing at least a portion of the set of data with the application so the portion of the set of data need not be acquired by the application.

These and other embodiments, aspects, advantages, and features of the present invention will be set forth in part in the description which follows, and in part will become apparent to those skilled in the art by reference to the following description of the invention and drawings or by practice of the invention. The aspects, advantages, and features of the invention are realized and attained by means of the instrumentalities, procedures, and combinations particularly pointed out in the appended claims.

DETAILED DESCRIPTION

Figure 1:
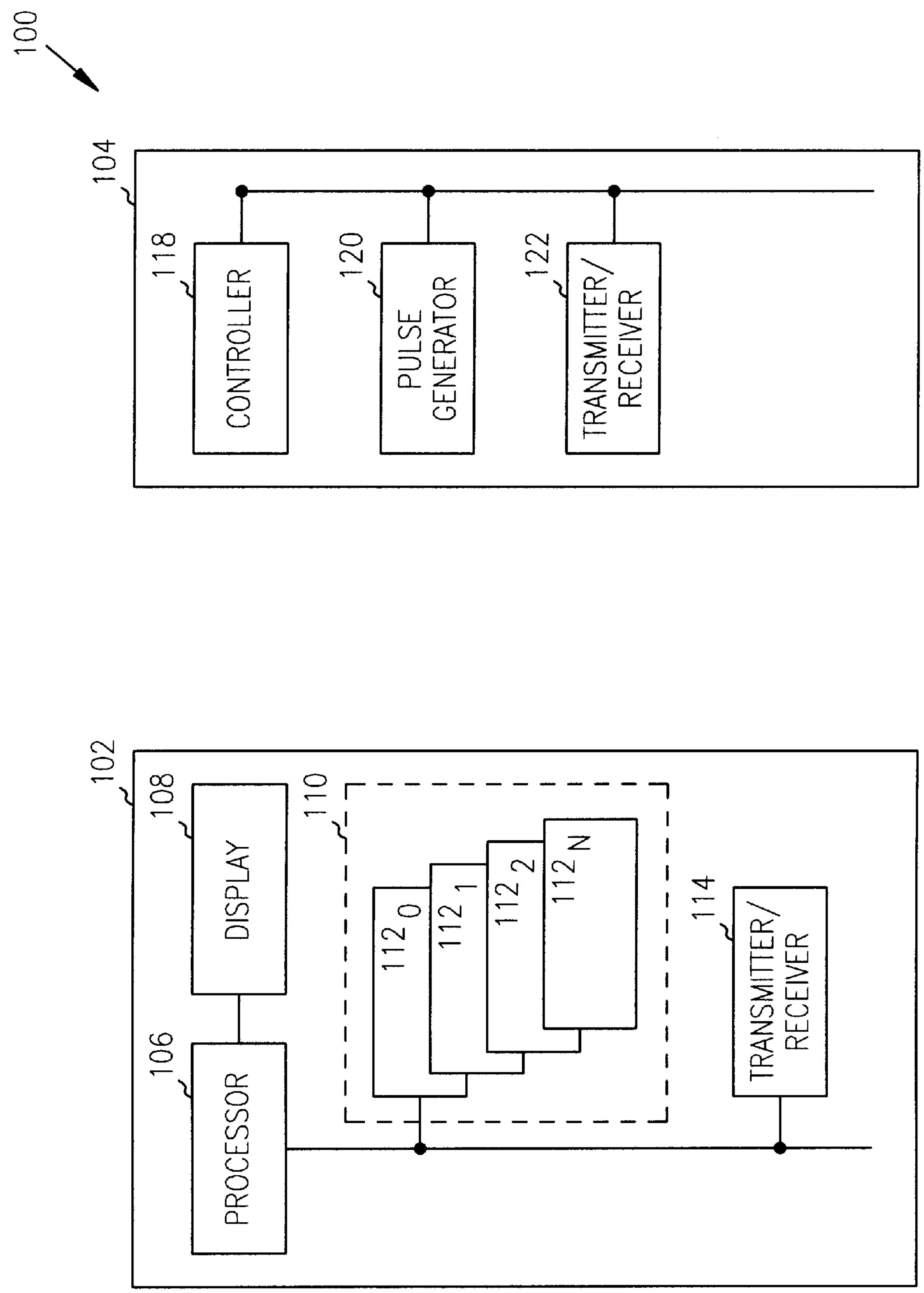
FIG. 1 is a block diagram illustrating a system in accordance with one embodiment.

In the following detailed description of the invention, reference is made to the accompanying drawings that form a part hereof, and in which are shown, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized and structural, logical, and electrical changes may be made without departing from the scope of the present invention.

The embodiments described herein focus on sharing information in a system that includes a programmer/recorder/monitor and an implantable medical device. The term information is understood to mean the inclusion of knowledge or data that has been generated or acquired. The ability to share information in the mentioned system eases the practice of a professional, such as a physician, who is making a diagnostic test or changing a therapy for a patient who has an implantable medical device, such as a pacemaker, implantable cardioverter defibrillator, or defibrillator.

An implantable cardioverter defibrillator is designed to detect and provide therapy for various types of arrhythmia including, ventricular tachycardia and ventricular fibrillation. The device may include a pulse generator to generate pulses that may be used in a therapy session. An external component, such as a programmer/recorder/monitor, allows interrogation and programming of the pulse generator, as well as access to the device's diagnostic features. The device can be programmed to provide a variety of detection options. The device can also provide noninvasive diagnostic testing and therapy history data. In one embodiment, the implantable cardioverter defibrillator may additionally function as a pacemaker.

FIG. 1 is a block diagram illustrating a system in accordance with one embodiment. System 100 includes a programmer/recorder/monitor 102 (hereinafter, programmer 102). The programmer 102 includes a processor 106 for controlling tasks, processes, and resources in the programmer 102. A display 108 is coupled to the processor 106. In one embodiment, a graphical user interface is presented on the display 108 to enable a professional, such as a physician, to operate the system 100.

The programmer 102 includes an environment 110 to execute applications $\mathbf{112}_0$, $\mathbf{112}_1$, $\mathbf{112}_2$, . . . , $\mathbf{112}_N$. In one embodiment, the environment 110 is an operating system. In one embodiment, applications $\mathbf{112}_0$, $\mathbf{112}_1$, $\mathbf{112}_2$, . . . , $\mathbf{112}_N$ include diagnostic test applications, configuration applications, electrogram display applications, and telemetry communication applications. In one embodiment, data that is generated or acquired from any of applications $\mathbf{112}_0$, $\mathbf{112}_1$, $\mathbf{112}_2$, . . . , $\mathbf{112}_N$ and can be shared with other applications $\mathbf{112}_0$, $\mathbf{112}_1$, $\mathbf{112}_2$, . . . , $\mathbf{112}_N$.

For illustrative purposes only, suppose a physician uses a configuration application to enter the intrinsic heart rate of a patient. Next, the physician wishes to run a diagnostic test application, such as a pace threshold test. Since the diagnostic test application also needs the intrinsic heart rate of the patient, the configuration application shares with the diagnostic test the intrinsic heart rate of the patient so that the physician need not re-enter that information. In another embodiment, the diagnostic test application determines that the configuration application contains information that it needs; in this case, the diagnostic test application accesses for its own use the information belonging to the configuration application.

In one embodiment, the sharing of information is carried out using common memory space that is accessible by all applications. In another embodiment, global variables that allow data to be shared by applications $\mathbf{112}_0$, $\mathbf{112}_1$, $\mathbf{112}_2$, . . . , $\mathbf{112}_N$ are used. Other embodiments may be used without departing from the present invention.

The programmer 102 includes a transmitter/receiver 114. The transmitter/receiver 114 allows the programmer 102 to communicate with the implantable medical device 104. The transmitter/receiver 114 may be used to issue instructions, initiate a diagnostic session, or program a therapy with the implantable medical device 104.

System 100 includes an implantable medical device 104. In one embodiment, the implantable medical device 104 is able, for a given patient, to detect and treat ventricular tachycardia or ventricular fibrillation with a combination of antitachycardia pacing, and monophasic or biphasic cardiovertion/debrillation shock therapy. In another embodiment, the implantable medical device 104 also detects and treats bradycardia conditions with pacing pulses in both the atrium and ventricle. In another embodiment, the implantable medical device 104 contains memory (not shown) that provides a record of patient data, therapy delivery counts, and a therapy history consisting of arrhythmia episode data, stored electrograms, and annotated intervals of tachyarrhythmic episodes.

The implantable medical device 104 includes a controller 118 to control tasks, processes, or resources within the implantable medical device 104. A pulse generator 120 is coupled to the controller 118. The pulse generator 118 generates pulses that are used in the treatment of arrhythmia detected by the implantable medical device 104. The device 104 also includes a transmitter/receiver 122. The transmitter/receiver 122 allows the implantable medical device 104 to receive instructions and program changes from the programmer 102. The transmitter/receiver 122 also allows the device 104 to send data back to the programmer 102. In one embodiment, the data that is sent back includes patient information, such as intrinsic heart rate, and therapy information, such as the frequency of therapy for a particular type of arrhythmia.

Figure 2:
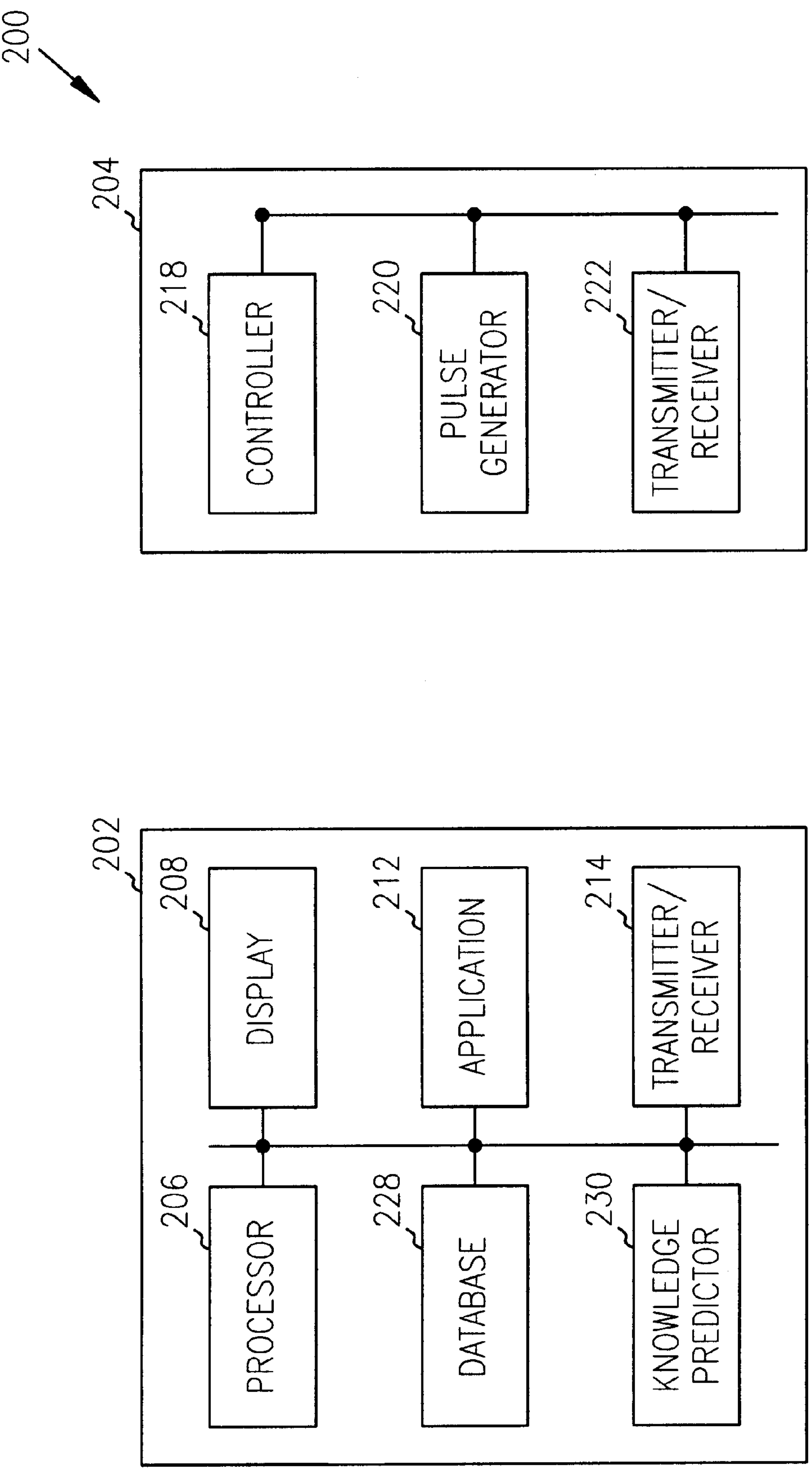
FIG. 2 is a block diagram illustrating a system in accordance with one embodiment.

FIG. 2 is a block diagram illustrating a system in accordance with one embodiment. FIG. 2 contains elements as described above (elements with the identical last two numerical digits) and so the above description regarding those elements is incorporated here. The programmer 202 includes a database 228. The database 228 contains information acquired in the operations of the implantable medical device 204. In one embodiment, the database queries the implantable medical device 204 for various pieces of information; the implantable medical device 204 in response to such query transmits to the database the requested information. In another embodiment, the processor 206 commands the implantable medical device 204 to send certain information to the database 228 so the information can be shared. In another embodiment, the implantable medical device 204 pushes information to the database 228 so the information can be shared. Other embodiments may be used without departing from the present invention.

The programmer 202 includes at least one application 212. In one embodiment, the application 212 is a software application executing in the programmer 202. In another embodiment, the application 212 is an integrated circuit in the programmer 202. In one embodiment, when the application 212 requires certain information, such as the lowest energy level of the pulse height that would capture the heart or heart rate of a patient, if the database 228 contains such information, the information would be shared with the application 212 by the database 228. In one embodiment, such sharing may be accomplished by the application 212 by making a structured-query-language (SQL) query to the database. This sharing would benefit a professional, such as a physician, from having to re-enter a set of data that is already present in the system 200.

The programmer 202 also includes an information predictor 230. In one embodiment, instead of residing on the programmer 202, the information predictor 230 may reside on the implantable medical device 204. The information predictor 230 operates to predict information that can be used by application 212. In one embodiment, such prediction is carried out by using a set of rules. In another embodiment, such prediction is made by using an expert system that has been trained to emulate a physician in the process of deriving or applying a diagnostic. In another embodiment, such prediction is carried out using a neural network with at least one layer of perceptrons.

For illustrative purposes only, in a diagnostic test called a pacing threshold test, suppose a physician would like to overdrive a patient's heart. It is possible that the database 228 does not contain the information to start the diagnostic test. If such is the case, the information predictor 230 may provide a suggested rate to the implantable medical device for starting the diagnostic test. Such suggested rate may be changed by the physician. Such suggested rate may be calculated by the information predictor 230 by looking at the patient's intrinsic heart rate (which may be available in the database 228) and formulating from that heart rate another higher rate with which the implantable medical device may safely overdrive the patient's heart. In one embodiment, the information predictor 230 determines when to look at the patient's intrinsic heart rate, such as looking at the rate during the diagnostic session with the patient, or upon entering the diagnostic test, or upon manual update by the physician. In another embodiment, the information predictor 230 has a set of rules that would not set a pacing rate higher than what the physician would normally allow the patient rate to get set to.

In yet another illustration, in a diagnostic test called an amplitude threshold test, suppose a physician would like to determine the lowest energy level of the pulses that would capture the heart or heart beat of a particular patient. The test is a tedious one for a physician to perform. However, operating the implantable medical device with low energy pulses is beneficial because it tends to increase the life of the device. In one example, the physician may start at 5 volts, decrement by 0.2 millivolts, wait for four or five beats to see if the implantable medical device loses capture, and then restart the test again until the lowest energy level can be determined. The information predictor 230 can alleviate such tedium by predicting the starting energy level at which to test the patient by looking at various factors that include the last level at which the test lost capture of the heart or heart beat. The physician benefits because such prediction narrows the range of energy levels that the physician would consider to determine the lowest effective energy level.

In one embodiment, the information predictor 230 predicts a pacing mode that a physician would want to use for various diagnostic tests, such as intrinsic amplitude test. Pacing mode is a well-known industry convention that does not limit the invention and thus will not be discussed here. In one embodiment, the information predictor 230 looks at the pacing history of the particular patient, and makes a suggestion to the physician regarding the starting pacing mode that has a greater than about 90 percent probability that a physician would have made the same suggestion.

Figure 3:
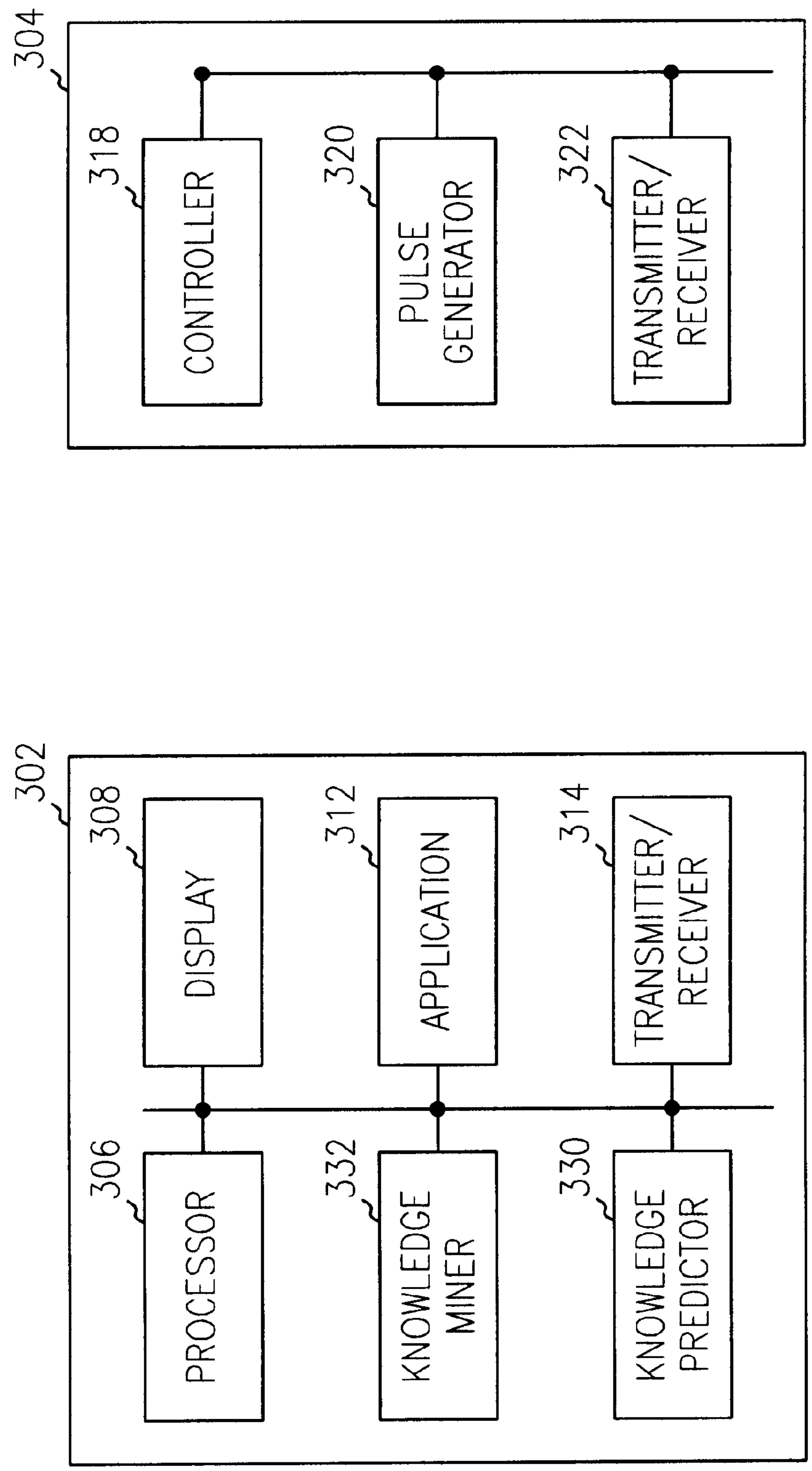
FIG. 3 is a block diagram illustrating a system in accordance with one embodiment.

FIG. 3 is a block diagram illustrating a system in accordance with one embodiment. FIG. 3 contains elements as described above (elements with the identical last two numerical digits) and so the above description regarding those elements is incorporated here. System 300 includes an information miner 332. In one embodiment, the information miner 332 interrogates the components of system 302, such as processor 306, display 308, and transmitter/receiver 314 to obtain information that may be reused in the system 300. In another embodiment, the information miner 332 interrogates the implantable medical device 304 and its components, such as the controller 318, the pulse generator 320, and transmitter/receiver 322 to obtain information that may be reused in the system 300.

When application 312 desires certain information, it may communicate with the information miner 332. If the information miner 332 contains the information desired by the application 312, it may share such information with the application 312 so that application need not acquire the information on its own.

In one embodiment, the information miner is implemented as an object executing in the programmer 302. Each component of the programmer 302 and the implantable device 304 may be wrapped by an object. These objects may share a common base class data structure with a virtual function that allows the information miner 332 to interrogate the components of the programmer 302 and the implantable device 304 when each object is instantiated and executed.

Figure 4:
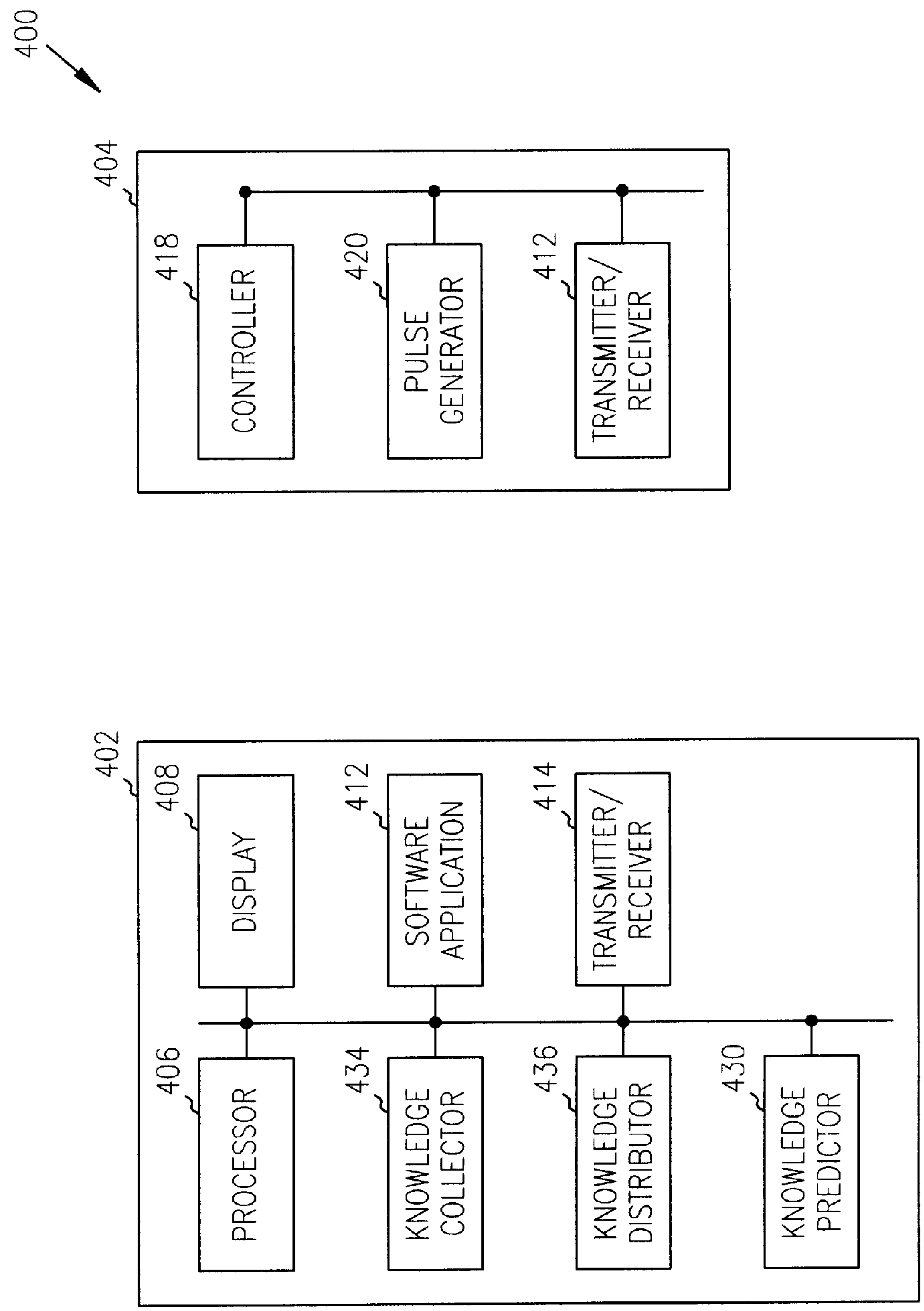
FIG. 4 is a block diagram illustrating a system in accordance with one embodiment.

FIG. 4 is a block diagram illustrating a system in accordance with one embodiment. FIG. 4 contains elements as described above (elements with the identical last two numerical digits) and so the above description regarding those elements is incorporated here. System 400 includes an information collector 434. The information collector 434 collects information generated by the programmer 402 and the implantable medical device 404. In one embodiment, when certain information generated or acquired by either the programmer 402 or the implantable medical device 404 should be shared, such as with application 412, the programmer 402 or the implantable medical device 404 forwards that information to the information collector 434 so it can be stored and retrieved later when needed.

System 400 also includes information distributor 436. The information distributor 436 distributes information collected by the information collector 434 to software application 412 and other components of programmer 402 or components of the implantable medical device 404. In one embodiment, the information distributor 436 detects whether the software application 412 needs certain information that may be made available by the information collector 434. In one embodiment, the implementation of this detection includes the ability of the information distributor 436 to determine that the software application 412 is being used by a professional, such as a physician. In another embodiment, the information collector 434, the information distributor 436, and the information predictor 430 are all objects in the sense of object-oriented technology.

Figure 5:
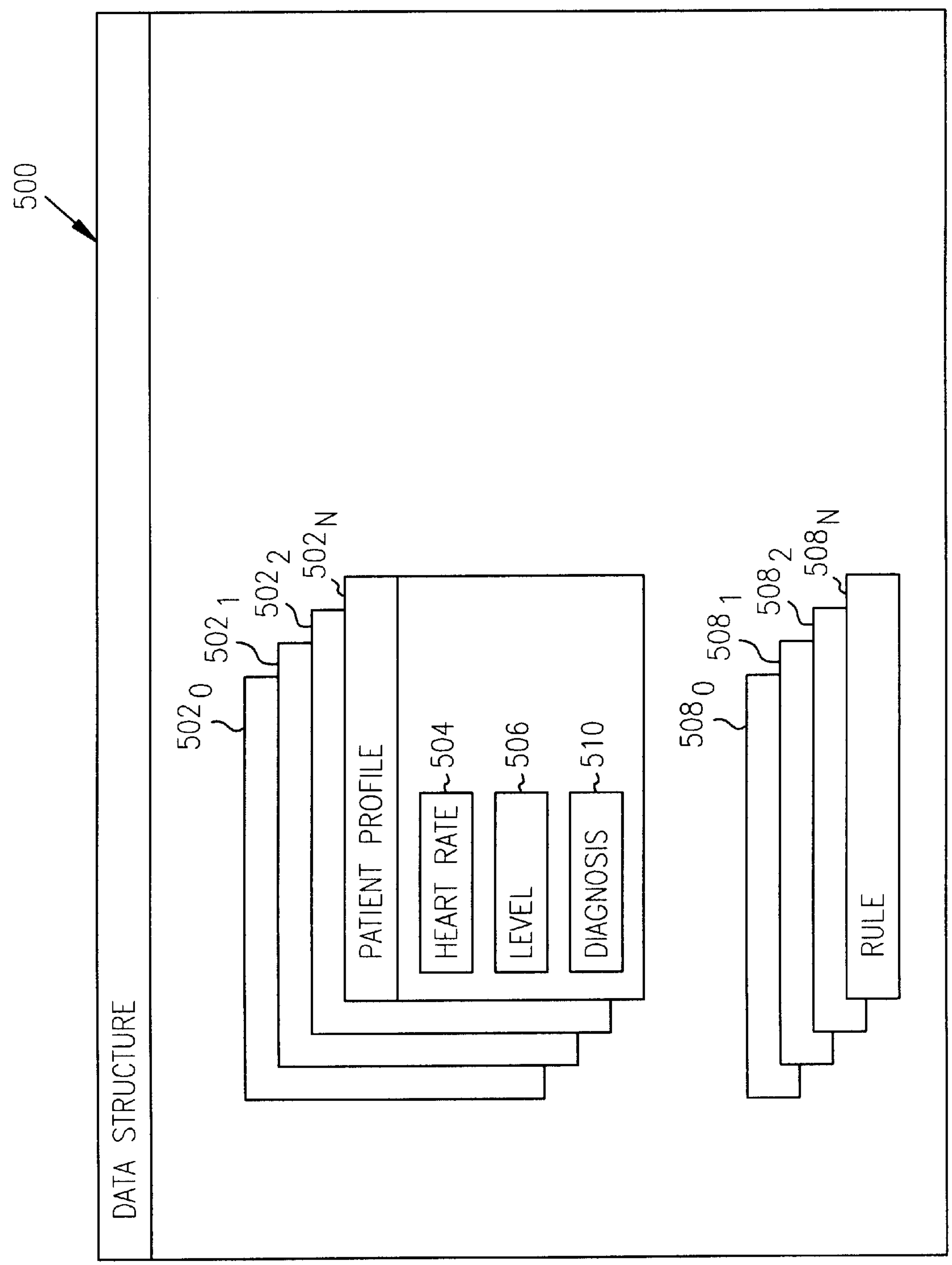
FIG. 5 is a block diagram illustrating a data structure in accordance with one embodiment.

FIG. 5 is a block diagram illustrating a data structure in accordance with one embodiment. Data structure 500 in one embodiment is a structure. In another embodiment, data structure 500 is a class. In another embodiment, data structure 500 is a linked list. Other embodiments may be used without departing from the present invention. The data structure 500 may reside either on the programmer or the implantable medical device.

The data structure 500 contains patient profile data structures $\mathbf{502}_0$, $\mathbf{502}_1$, $\mathbf{502}_2$, . . . , $\mathbf{502}_N$. Each patient profile data structure contains information that is particular to one patient. The data structure $\mathbf{502}_N$ includes a heart rate data type 504 to store the heart rate of a patient. In one embodiment, the heart rate that is stored is the intrinsic heart rate. The data structure $\mathbf{502}_N$ includes a level data type 506 to store a level of energy of the pulses applied to the patient. In one embodiment, the lowest energy level is stored here. In another embodiment, the last applied level in the amplitude threshold test is stored here. The data structure $\mathbf{502}_N$ also includes a diagnosis data type 510. In one embodiment, this data type 510 stores at least one arrhythmia diagnosis determined by a physician, such as atrial tachycardia. This data type 510 can be used by an information predictor to predict a particular pacing mode to suggest to a physician during a diagnostic test.

In one embodiment, the data structure 500 may also contain a set of rules $\mathbf{508}_0$, $\mathbf{508}_1$, $\mathbf{508}_2$, . . . $\mathbf{508}_N$. In another embodiment, this set of rules exists separately from the data structure 500. When a value of an instantiation of a data type in data structure 500 or data structure $\mathbf{502}_N$ is shared in the system that includes an implantable medical device, the set of rules is applied. The term "instantiation" is understood to mean the inclusion of forming a variable from a data type during the execution of software in the system. The term "value of an instantiation" means the content of a variable formed from a data type during the execution of software in the system.

For illustrative purposes only, when a pacing threshold test is performed, the test uses the value stored in a variable formed from the heart rate data type 504 of patient profile data structure $\mathbf{502}_N$; the value represents the intrinsic heart rate of the patient; at least one rule from the set of rules $\mathbf{508}_0$, $\mathbf{508}_1$, $\mathbf{508}_2$, . . . $\mathbf{508}_N$ is applied to add 10 beats per minute to the intrinsic heart rate so as to overdrive the patient's heart.

Figure 6:
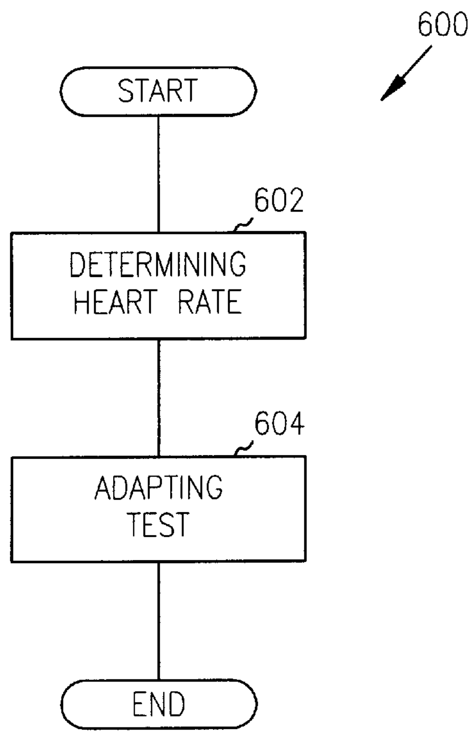
FIG. 6 is a flow diagram illustrating a method in accordance with one embodiment.

FIG. 6 is a flow diagram illustrating a method in accordance with one embodiment. The process 600 is a process for adapting a pacing threshold test. The process 600 begins at block 602 where the patient's intrinsic heart rate is determined. Next, in block 604, the information gained in the process at block 602 is adapted according to a set of rules. In one embodiment, these rules determine the next level of heart rate to pace the patient so as to obtain 100 percent pacing drive.

Figure 7:
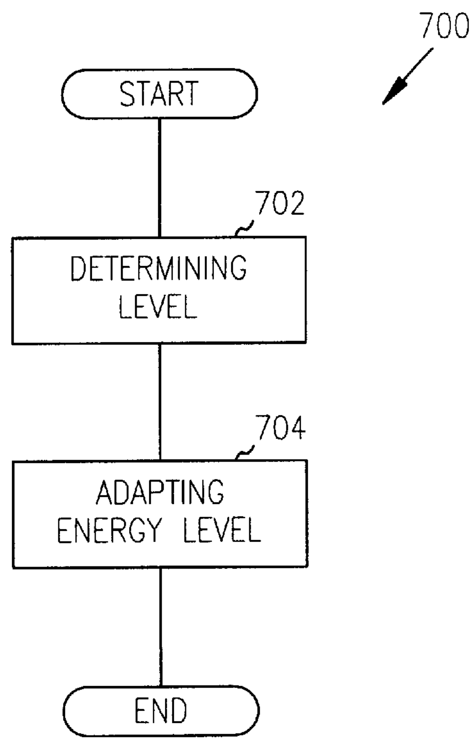
FIG. 7 is a flow diagram illustrating a method in accordance with one embodiment.

FIG. 7 is a flow diagram illustrating a method in accordance with one embodiment. The process 700 is a process for adapting an amplitude threshold test. The process 700 begins at block 702 where the energy level that was previously applied by the test is determined. Next, at block 704, a set of rules is applied to the information gained at block 702. In one embodiment, this set of rules adapts the energy level determined at block 702 to another energy level that would enable the physician to more efficiently localize the lowest energy level that would capture the heart or heart rate or heart beat of the patient.

Figure 8:
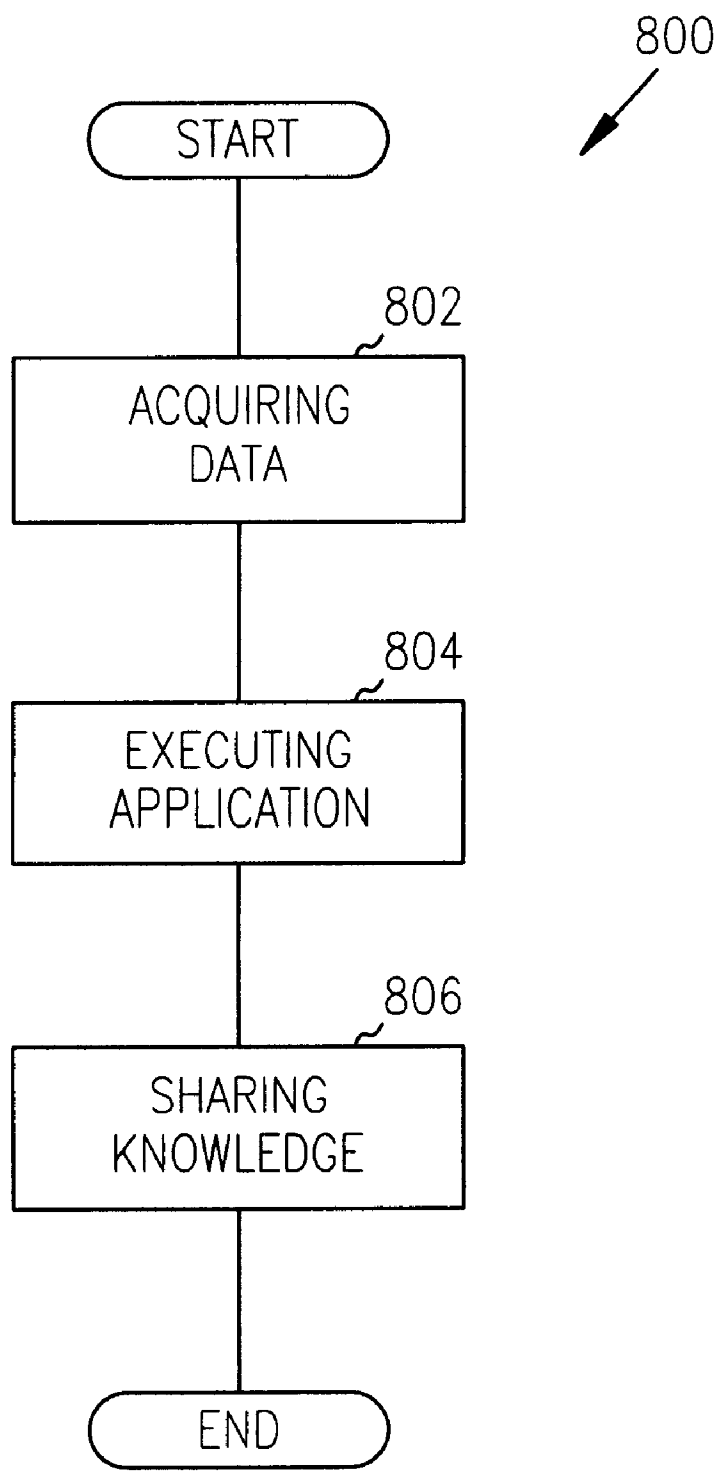
FIG. 8 is a flow diagram illustrating a method in accordance with one embodiment.

FIG. 8 is a flow diagram illustrating a method in accordance with one embodiment. The process 800 begins at block 802 where data is acquired. In one embodiment, data is acquired as the result of a professional, such as a physician, keying in data. values for an application running on a programmer to program an implantable medical device. In another embodiment, data is acquired as a result of the operations of a programmer or an implantable medical device.

Next, at block 804, a software application is executed. However, the software application desires data that was obtained at block 802. At block 806, the data obtained at block 802 is shared with the software application. In one embodiment, a set of rules is applied when the data is shared with the software application. In another embodiment, a set of rules is applied to modify the data before it is shared with the software application.

Figure 9:
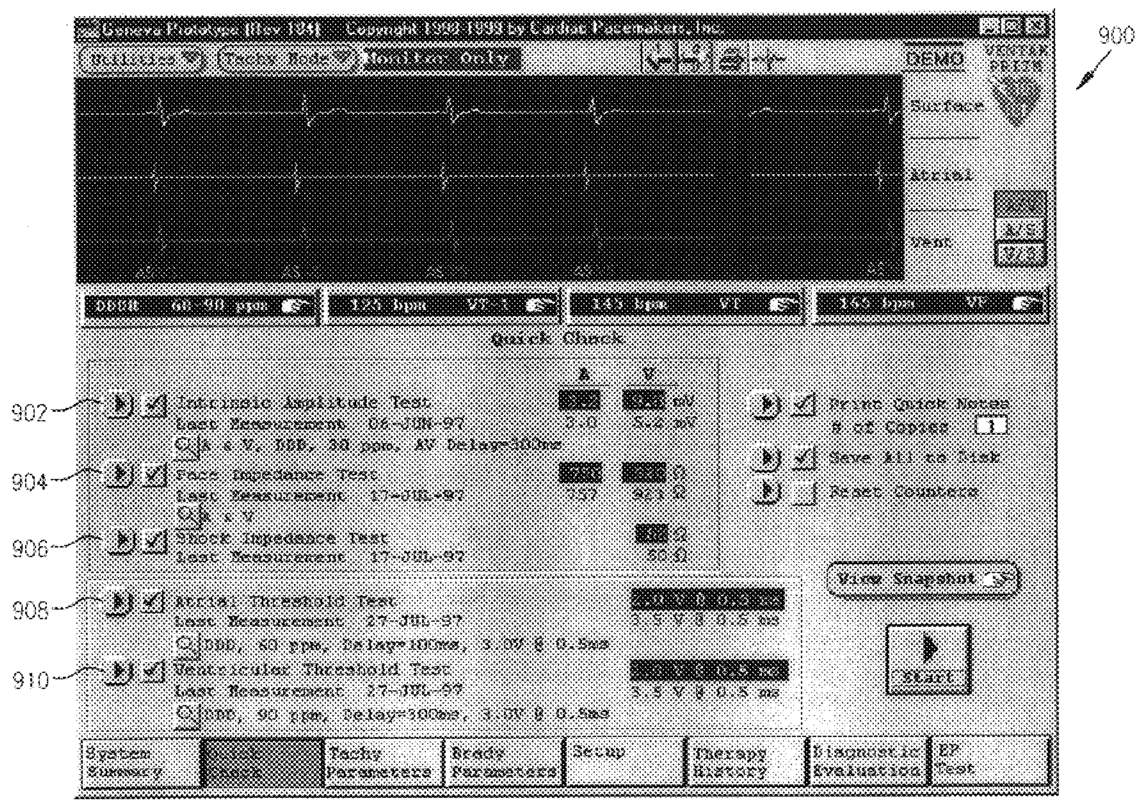
FIG. 9 is a pictorial diagram illustrating a display in accordance with one embodiment.

FIG. 9 is a pictorial diagram illustrating a display in accordance with one embodiment. Display 900 shows a user interface view of the various diagnostic tests, such as intrinsic amplitude test 902, pace impedance test 904, shock impedance test 906, atrial threshold test 908, and ventricular threshold test 910. The data acquired or generated by these tests may be shared, predicted, or adapted among them as described heretofore.

Figure 10:
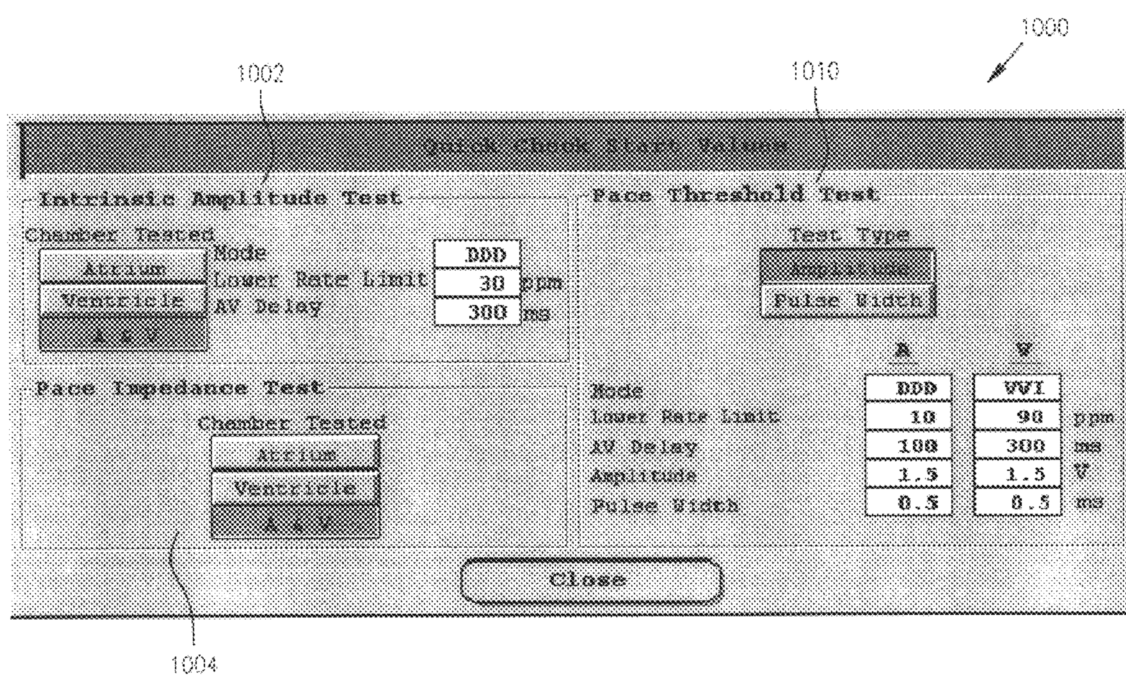
FIG. 10 is a pictorial diagram illustrating a display in accordance with one embodiment.

FIG. 10 is a pictorial diagram illustrating a display in accordance with one embodiment. The display 1000 shows another user interface with respect to the starting values of the intrinsic amplitude test 1002, pace impedance test 1004, and pace threshold test 1010. The starting data in the dialog boxes of these tests may be shared, predicted, or adapted among them as described heretofore.

Conclusion

Thus, systems, structures, and methods have been described for sharing information in systems that include implantable medical devices.

Although the specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention. It is to be understood that the above description is intended to be illustrative and not restrictive. Combinations of the above embodiments and other embodiments will be apparent to those of skill in the art upon reviewing the above description. The scope of the invention includes any other applications in which the above structures and fabrication methods are used. Accordingly, the scope of the invention should only be determined with reference to the appended claims, along with the full scope of equivalents to which such claims are entitled.

What is claimed is:

1. A system that includes an implantable medical device implanted in a patient, the system comprising:

a first application executing a first diagnostic test, wherein the first application acquires a set of data from the implantable medical device in executing the first diagnostic test; and a second application initiating the execution of a second diagnostic test, wherein the first application shares a portion of the set of data acquired by the first application in executing the first diagnostic test with the second application so that the second application need not acquire the portion of the set of data.

2. The system of claim 1, wherein the second diagnostic test is performed on the patient using the implantable medical device.

3. The system of claim 2, wherein the second diagnostic test is a pace threshold test.

4. The system of claim 2, wherein the second diagnostic test is a level threshold test.

5. A system that includes an implantable medical device implanted in a patient, the system comprising:

a first application executing a first diagnostic test, wherein the first application acquires a set of data from the implantable medical device in executing the first diagnostic test; and a second application initiating the execution of a second diagnostic test, wherein the second application uses a portion of the set of data acquired by the first application in executing the first diagnostic test so that the second application need not acquire the portion of the set of data in the execution of the second diagnostic test.

6. The system of claim 5, wherein the first diagnostic test is performed on the patient using the implantable medical device.

7. The system of claim 6, wherein the first diagnostic test is a pace threshold test.

8. The system of claim 6, wherein the first diagnostic test is a level threshold test.

9. A system that includes an implantable medical device implanted in a patient, the system comprising:

a database to store a set of data acquired from the implantable medical device; and an application executing on the system, wherein the database shares a portion of the set of data acquired in operating the implantable medical device so that the application need not acquire the portion of the set of data.

10. The system of claim 9, wherein the system further comprises an information predictor to generate input information for the application executing on the system, wherein the information predictor predicts the input information based on a type of the application and the patient.

11. The system of claim 9, wherein the application is a diagnostic test that is performed on the patient using the implantable medical device.

12. The system of claim 11, wherein the diagnostic test is a pace threshold test.

13. The system of claim 11, wherein the diagnostic test is a level threshold test.

14. A system that includes an implantable medical device implanted in a patient, the system comprising:

an information miner to mine information generated in the system that includes the implantable medical device;

an application executing on the system, wherein the desire of the application for a portion of the information mined by the information miner is detected, wherein the information miner shares the portion of the information mined by the information miner so that the application need not acquire the portion of the information.

15. The system of claim 14, wherein the system further comprises an information predictor to generate input information for the application executing on the system, wherein the information predictor predicts the input information based on a type of the application and the patient.

16. The system of claim 14, wherein the application is a diagnostic tests that is performed on the patient using the implantable medical device.

17. The system of claim 16, wherein the diagnostic test is a pace threshold test.

18. The system of claim 16, wherein the diagnostic test is a level threshold test.

19. The system of claim 14, wherein the information miner detects the need of the application for the portion of the information mined by the information miner.

20. The system of claim 14, wherein the application identifies the information needed by the application to the information miner, wherein the information miner shares the portion of the information mined by the information miner so that the application need not acquire the portion of the information.

21. A system that includes an implantable medical device implanted in a patient, the system comprising:

an information collector to collect information generated in the system that includes the implantable medical device;

an information distributor coupled to the information collector to distribute information;

a software application executing on the system, wherein the information distributor detects the need of the software application for a portion of the information collected by the information collector, wherein the information distributor shares the portion of the information collected by the information collector so that the software application need not acquire the portion of the information.

22. The system of claim 21, wherein the system further comprises an information predictor to generate input information for the software application executing on the system, wherein the information predictor predicts the input information based on a type of the software application and the patient.

23. The system of claim 22, wherein the information predictor is an object executing in the system.

24. The system of claim 21, wherein the application is a diagnostic test that is performed on the patient using the implantable medical device.

25. The system of claim 24, wherein the diagnostic test is a pace threshold test.

26. The system of claim 22, wherein the diagnostic test is a level threshold test.

27. The system of claim 21, wherein the information collector is an object executing in the system.

28. The system of claim 21, wherein the information distributor is an object executing in the system.

29. A data structure to share information in a system including an implantable medical device implanted in a patient, the data structure comprising:

at least one patient profile data structure that includes a plurality of data types, the at least one patient profile data structure including:

a heart rate data type to store the heart rate of the patient; and a level data type to store a level of energy that was previously applied by the implantable medical device to the patient; and at least one rule to be applied when a value of an instantiation of a data type from the plurality of data types of the at least one patient profile data structure is shared in the system.

30. A data structure to share information in a system including an implantable medical device implanted in a patient, the data structure comprising:

at least one patient profile data structure that includes a plurality of data types, the at least one patient profile data structure including:

a heart rate data type to store the heart rate of the patient; and a level data type to store a level of energy that was previously applied by the implantable medical device to the patient;

a patient diagnosis data type to store at least one arrhythmia diagnosis for the patient;

at least one rule to be applied when a value of an instantiation of a data type from the plurality of data types of the at least one patient profile data structure is shared in the system.

31. A method of performing a pacing threshold test in a system that includes an implantable medical device implanted in a patient, the method comprising:

sharing an intrinsic heart rate of the patient acquired by a previously-executed application with a presently-executed application to perform the pacing threshold test so that the presently-executed application need not acquire the intrinsic heart rate; and adapting the pacing threshold test by the system based on the intrinsic heart rate of the patient.

32. A method of performing an energy level threshold test, the method comprising:

determining an energy level when the energy level threshold test was previously executed; and adapting the energy level threshold test based on the energy level when the energy level threshold test was previously executed.

33. A method of sharing information in a system that includes an implantable medical device, the method comprising:

acquiring a set of data;

executing an application; and sharing at least a portion of the set of data with the application so the portion of the set of data need not be acquired by the application.

34. The method of claim 32, wherein sharing at least a portion of the set data further comprises predicting a new set of data for the diagnostic test to use.

* * * * *

UNITED STATES PATENT AND TRADEMARK OFFICE

CERTIFICATE OF CORRECTION

PATENT NO. : 6,405,086 B1
DATED : June 11, 2002
INVENTOR(S) : Conley et al.

It is certified that error appears in the above-identified patent and that said Letters Patent is hereby corrected as shown below:

Title page,
Item [56], References Cited, U.S. PATENT DOCUMENTS, insert

| | | |
|---|---|---|
| -- 5,511,553 | 4/1996 | Segalowitz ..........128/696 |
| 5,833,623 | 11/1998 | Mann et al. ..........600/523 |
| 5,843,138 | 12/1998 | Evers et al. ..........607/30 --. |

Column 9,
Line 59, delete "tests" and insert -- test --, therefor.

Signed and Sealed this

Twelfth Day of November, 2002

*Attest:*

JAMES E. ROGAN

*Attesting Officer* *Director of the United States Patent and Trademark Office*